United States Patent [19]

Nakai

[11] 4,333,471
[45] Jun. 8, 1982

[54] NIPPLE COVER

[75] Inventor: Tadanobu Nakai, Kita-Katsuragi, Japan

[73] Assignee: Tokiwa Chemical Industries, Limited, Osaka, Japan

[21] Appl. No.: 226,446

[22] Filed: Jan. 19, 1981

[51] Int. Cl.³ .......................... A61J 13/00; A41C 3/06
[52] U.S. Cl. ...................................... 128/505; 128/150
[58] Field of Search ............... 128/150, 252, 505, 360, 128/132, DIG. 15

[56] References Cited

U.S. PATENT DOCUMENTS 2,292,024  8/1942  Dreher ................................ 128/505
3,280,818  10/1966  Pankey et al. ..................... 128/505

Primary Examiner—Doris L. Troutman
Attorney, Agent, or Firm—Nathaniel A. Humphries

[57] ABSTRACT

A disc-shaped nipple cover has a flexible paper backing sheet covered with pressure sensitive adhesive and a central soft feld pad. Release paper coverings protect the nipple cover until removal prior to usage.

4 Claims, 3 Drawing Figures

NIPPLE COVER

BACKGROUND OF THE INVENTION

This invention relates to a new and unique covering device for women's nipples and is particularly directed to a new, unique and attractive device of the type similar to an adhesive bandage of the type used for first-aid treatment of the skin, which device is especially adapted to conceal women's nipples and which is basically simple in construction and consequently economical to manufacture.

Women normally wear a brassiere or the like on their breasts in order to provide a pleasing contour by the effect of moderate pressure provided by the brassiere. However, in the hot summer season when women customarily wear thin clothes, the brassiere is visible through thin cloth upper garments which can present a rather unsightly appearance. Also, the brassiere presses upon the breasts and body of the user by its belts and straps with a resultant inherent discomfort and inconvenience. Moreover, the use of a brassiere can be very uncomfortable during hot weather and can cause excessive perspiration to the discomfort of the user.

BRIEF DESCRIPTION OF THE INVENTION

The present invention was developed with an aim of eliminating the above disadvantages, and the invention provides an attractive nipple-cover in the form of a small sheet of paper not requiring belts and straps which is consequently unlike a brassiere. The invention can be used sufficiently by only placing it on the nipples and surrounding areas of the breasts, and the wearer feels comfortable and cool, since the nipple-cover is made of a sheet of paper having an excellent air permeability so as to provide cooling evaporation of perspiration.

It is therefore the primary object of the invention to provide a new and unique covering device adapted suitably to conceal women's nipples and capable of effecting evaporation of perspiration freely.

Another object of the invention is to provide a new, unique and attractive covering device for women's nipples which is simple in construction, economical to produce, easy to use and is also ornamental in appearance.

These and other objects and advantages of the invention will become apparent from the following description and the accompanying drawings, in which:

DETAILED DESCRIPTION OF THE INVENTION

Figure 1:
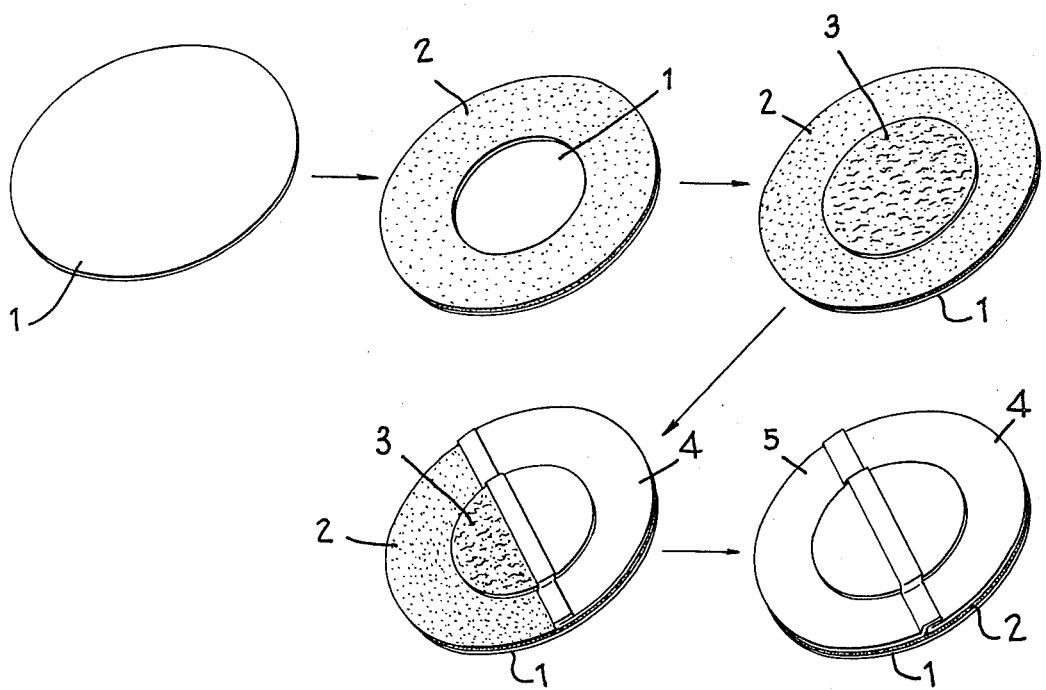
FIG. 1 is a perspective view of the production process of the invention.

Turning to the embodiment as illustrated in FIG. 1, the main element of the invention comprises a flexible sheet of paper backing 1 having an excellent air permeability and which is formed in a circular configuration and a layer of tacky and pressure sensitive adhesive agent 2 of the type used on bandages is applied annularly on one surface of the paper backing 1 along an entire peripheral portion thereof. A centrally disposed circular-shaped disc of soft felt fabric 3 of a dimension exceeding a little over an inner circumferential edge portion of the adhesive coating layer 2 is secured at its peripheral edge portion to said adhesive coating layer 2. A pair of inner and outer protective cover release papers 4 and 5 of semi-circular configuration have a diameter equal to that of the paper backing and are provided for covering the felt fabric 3 and are secured at arcuate edge portions to the adhesive coating layer 2. Cover release papers 4 and 5 are overlapped one above the other at each inner diametric edge and inner release paper 4 is turned up and folded at the inner diameter edge portion thereof as shown in FIG. 1.

Figure 3:
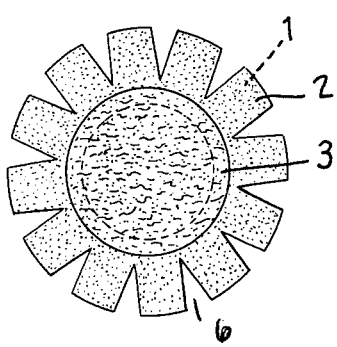
FIG. 3 is a front view of another embodiment of the invention with release papers peeled off.
Figure 2:
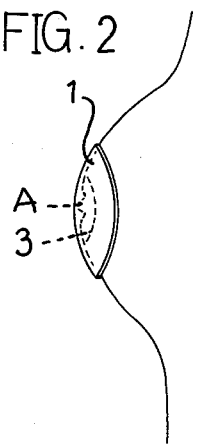
FIG. 2 is a side view showing the state of use of the invention.

As shown in FIG. 3, the peripheral edge portion of the paper backing is provided with indentation cuts 6 so that it avoids the formation of wrinkles or creases when it is placed on the nipple and secured to the user's skin.

The invention as described above is used by first peeling the outer release paper 5 which is first removed and the inner release paper 4 is then peeled off prior to use. The felt fabric 3 is placed on the nipple A to conceal it and the pressure sensitive adhesive coating layer 2 is pressed down in order to be secured to the surrounding skin of the user.

The nipple-cover of the present invention as described above, unlike the customary brassiere, is free from any pressure given to the breasts by its belts and the like, and the application of the same to the nipples is simple and easy since the nipple-cover is provided with the soft felt fabric on the flexible and good permeable sheet of paper backing, and the product thus fabricated induces absorption of perspiration and is beneficial for health. Further, the invention presents an ornamental appearance and engenders a good feeling on the part of the user.

I claim:

1. A nipple-cover in the form of a sheet of paper for covering women's nipples comprising a flexible paper backing having an excellent air permeability, a coating layer of tacky and pressure sensitive adhesive composition united to one surface of said paper backing, a felt fabric member centrally disposed on said one surface, a pair of protective cover release papers for covering said felt fabric arranged to lie one above the other at adjacent edge portions thereof with one edge of an inner release paper being turned up and folded.

2. A nipple-cover of claim 1 wherein said paper backing is of circular shape.

3. A nipple-cover of claim 2 wherein said circular-shaped paper backing is provided with indentation cuts on its entire peripheral edge.

4. A nipple-cover of claim 1 wherein said adhesive coating layer is applied annularly along a marginal edge portion on said one surface of the paper backing.

* * * * *